United States Patent [19]

Legario et al.

[11] Patent Number: 5,438,000
[45] Date of Patent: Aug. 1, 1995

[54] SERUM SEPARATION SEALANT

[75] Inventors: Ronald Legario, Suita; Toshiomi Nakamura, Yokohama; Toshiko Shibata, Ichikawa, all of Japan

[73] Assignee: Nippon Paint Co., Ltd., Osaka, Japan

[21] Appl. No.: 151,199

[22] Filed: Nov. 12, 1993

[30] Foreign Application Priority Data

Nov. 12, 1992 [JP] Japan .................. 4-302405
Nov. 5, 1993 [JP] Japan .................. 5-276288

[51] Int. Cl.⁶ .............................................. B01D 21/26
[52] U.S. Cl. ........................................ 436/17; 436/18; 435/2; 106/266; 252/60; 210/511
[58] Field of Search ............ 436/8, 174, 17, 18; 435/2; 210/510-518, 927, 789; 106/266; 252/60

[56] References Cited

U.S. PATENT DOCUMENTS

| | | | |
|---|---|---|---|
| 3,780,935 | 12/1973 | Lukacs et al. | 233/1 A |
| 4,071,316 | 1/1978 | Wright | 23/230 B |
| 4,083,784 | 4/1978 | Zine, Jr. | 210/83 |
| 4,189,328 | 2/1980 | Flores | 106/288 |
| 4,457,782 | 7/1984 | Honda et al. | 106/266 |
| 4,534,798 | 8/1985 | Honda et al. | 106/266 |
| 4,770,779 | 9/1988 | Ichikawa et al. | 210/516 |
| 4,994,393 | 2/1991 | Pradham et al. | 436/8 |
| 5,079,002 | 1/1992 | Nagai et al. | 424/400 |
| 5,169,543 | 12/1992 | Shibata | 210/789 |

FOREIGN PATENT DOCUMENTS

| | | |
|---|---|---|
| 0046391 | 2/1982 | European Pat. Off. . |
| 0384331 | 8/1990 | European Pat. Off. . |
| 2743882 | 8/1978 | Germany . |
| 125026 | 5/1989 | Japan .................. G01N 33/48 |

OTHER PUBLICATIONS

Patent Abstracts of Japan, Abstract of JP 59-129216.

*Primary Examiner*—David A. Redding
*Attorney, Agent, or Firm*—Sughrue, Mion, Zinn, Macpeak & Seas

[57] ABSTRACT

A serum separating sealant having a specific gravity at 20° C. of 1.035 to 1.065, a viscosity of 100 to 400 Pa.S and a yield stress of 100 to 400 dyne/cm² and comprising:

(A) 100 parts by weight of a polymer having specific gravity at 20° C. of 0.94 to 1.06 and a viscosity of 10 to 140 Pa.S, derived from an alkyl acrylate or alkyl methacrylate monomer having the formula (I):

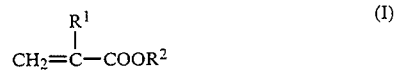

wherein $R^1$ denotes H or $CH_3$, $R^2$ denotes an alkyl group having 1 to 18 carbon atoms;

(B) 0.5 to 10 parts by weight of at least one component selected from silica and bentonite; and (C) 0.01 to 2 parts by weight of at least one surfactant selected from the group consisting of:
  (C-1) fluorocarbon-based surfactants;
  (C-2) polyester modified alkylpolysiloxane based surfactants.

12 Claims, No Drawings

SERUM SEPARATION SEALANT

BACKGROUND OF THE INVENTION

1. Field of the Invention

The present invention relates to a serum separation sealant. More specifically, it relates to a serum separation sealant having an excellent balance of flow and specific gravity characteristics and an excellent storage stability.

2. Description of the Related Art

Recently, clinical analytical technologies detecting minute amounts of the intended biochemical substances have made remarkable advances. For this purpose, there have been demands for improved techniques of separating whole blood into the constituent components thereof, i.e., serum and blood cells. It is required in the above-mentioned analytical technologies that the separated serum portion should be free of any red blood cells which could affect the clinically measured data.

The present invention emplores the use of a thixotropic gelatinous material, dispensed in a test tube, in which blood (or blood plasma) is collected. Under the influence of a centrifugal force, the gelatinous material moves to a region between the upper serum (or plasma) and the lower solid blood clot portion due to the differences in the specific gravities, forming a partitioning barrier. The serum is then collected for clinical analysis. The formation of an effective barrier which separates the constituents and prevents the diffusion of blood cells back into the serum (or plasma) portion is the major function of a serum separator. Such a material must flow only under the influence of centrifugal force and maintain its dispensed position between the serum layer and the clot layer when the centrifugal force is relieved. For example, if the test tubes are tilted on their side, it is desirable for the separator material to maintain its position, whereby the blood cell portion does not flow and the partitioning barrier is not broken with the lapse of days. This is especially important during transport or storage where the tubes may be subjected to such positions. Excessive flowability would render the tubes useless.

The most suitable material for such a purpose possesses structural viscous properties, which is called thixotropic fluid properties, which impart a solid like behaviour during transient periods, and can break down during centrifugation, losing its solid properties, allowing for flow to occur. At the end of centrifugation, the gelatinous material has the ability to rebuild its network structure and retain its previous solid properties. Serum separators using such a principle were first suggested by U.S. Pat. No. 3,780,935 (Lukacs et al.) and U.S. Pat. No. 4,071,316 (Wright et al.), and consist of a network forming silica powder dispersed in a diorganosiloxane resin.

In these serum separatoes rheology and specific gravity were controlled according to polymer properties and silica contents. However, over extended storage periods, the silicone polymer had a tendency to react completely with the silica surface, resulting in reduced thixotropy. In other words, the mixture loses its solid like properties which results in a weakened barrier. To achieve appropriate thixotropy, high silica content was required. However, gels with excessive silica content tend to be hardened with time which was found to be detrimental to movement during centrifugation. Moreover, silicone polymers are expensive and difficult in adjusting properties of viscosity and specific gravity.

To alleviate the above-mentioned instability of the separation sealant of the prior art, Honda et al. (U.S. Pat. No. 4,534,798) have suggested the use of a polymer combination consisting of epoxy modified vegetable or animal oil and liquid chlorinated paraffins or liquid polyolefins. The epoxy modified vegetable/animal oil can form a strong association with silica powders and enhance the thixotropic properties. Liquid chlorinated paraffins or polyolefin constituents serve as a medium for dispersion. However, thixotropic properties were still rather low and required high polymer viscosities in order to attain barrier strength, making such gels difficult to work with during the production of gelatinous materials and the dispensing thereof into tubes.

In relation to silicone polymers, U.S. Pat. No. 4,083,784 (Zine, Jr.) implied the use of, as a third component, polysiloxane-polyoxyalkyl copolymer, which when added in sufficient amounts, competed with the main silicone polymer for reaction with the silica filler and maintained the required thixotropy over a long time. An added effect of this agent is to further enhance the thixotropic properties. Ichikawa et al. (U.S. Pat. No. 4,770,779) also entail using the same type of polysiloxane polymer, as a thixotropic agent, in a composite mixture of $\alpha$-olefin-dimaleate copolymer and bentonite powder or silica. Another effect of using this thixotropic agent is the reduction in the concentration of network forming agents such as Aerosil and Bentonite powder.

Another example cited in U.S. Pat. No. 4,994,393 (Pradhan et al.) discloses the use of a dual resin system consisting of poly-$\alpha$-pinene polymer and chlorinated hydrocarbons, a "network stabilizer" or thixotropic agent (e.g., glycerol, ethylene diamine, propylene glycol or ethylene glycol), and fumed silica or titanium dioxide. In this composition, the pinene resin per se had a low specific gravity and required addition of a chlorinated hydrocarbon resin to adjust to the desired level of the specific gravity. Consequently, when the polymer having a low specific gravity is mixed with immiscible resin for the adjustment of the specific gravity, gelatinous materials floating on the serum surface tend to be formed. This is especially prevalent when the material is stored over long periods of time and/or under severe conditions of 60° C. or more, which can be encountered during transportation. In such cases, the mixture tends to be precipitated out of the dissolution conditions, due to immiscibility between silica powder and polymer. If there are components with a specific gravity less than the serum (s.g. = 1.022–1.032), such as pinene and polysiloxane resin, they would have a strong tendency to break away from the main barrier body and float on the serum surface. Such a phenomena has no effect on immunoassay data, but has been proven to be a hindrance during analytical procedures.

JP-B-1-1-25026 discloses gelatinous materials. When a blood collecting tube is filled in advance with said gelatinous materials, it is preferable to use a material with a structural viscosity such that it will not flow in the distribution stage. On the other hand, when separating the blood, it is necessary to apply as small a centrifugal force (for example, less than 1500G) as possible in a short time (for example, less than 10 minutes) so as to prevent and to suppress effects of hemolysis on the clinical examination values. To promote movement of the gelatinous materials and form a barrier under a low centrifugal force, it is preferable that the viscosity of the gelatinous materials be low. The barrier of the gelatinous material, formed under centrifugation, must be sturdy or firm to prevent breakdown during the decantation of the serum. Thus, it is necessary that the gelatinous material possess transport stability and partitioning ability and also exhibits excellent movability.

As mentioned earlier, some gelatinous materials tend to "harden" with time, resulting in highly viscous materials, thus making movement difficult to achieve. To improve reliability, U.S. Pat. No. 4,189,382 (Zine, Jr.) suggests the insertion of a cylindrical like object, referred to as an "Energizer", inside the gel tube, after dispensing. Its main function is to apply extra force on the gel body, at the onset of centrifugation, and initiate movement. It can also serve as a carrier for clotting agents. Similar proposals have been made, using glass beads. U.S. Pat. No. 4,770,779 (Ichikawa et al.) suggests a specialized gel dispensing method such that a cone like cavity is formed on the upper surface. Such a condition, by virtue of the centrifugal force, also promotes the gel to readily flow. While these procedures are effective at maintaining reliability (or barrier formation), they require extra steps during dispensing, and add to the overall cost of the gel tube.

A practical requirement of the gelatinous materials is that they should exhibit little or no free flow properties, during transitory periods, regardless of the gel-containing tube position. It should maintain the initial dispensed position thereof, before actual use. If the gel exhibits excessive free flow, it could coat the entire tube surface, leading to remnant red blood cells adhering to the tube wall, on the serum side of the barrier. Furthermore, gel tubes, under this condition, tend to form weak or incomplete barriers. To minimize free flow, extra precaution must be taken to maintain the gel tubes in an upright position, for up to one day, upon completion of the dispensing procedure. This allows the networking to reform and retain its solid properties, broken down during the dispensing process. This again has shown to be a cumbersome procedure. Free flow can be inhibited by adjusting the gel formulation to achieve high "yield stresses", which is the minimum force per square unit area, required to make the gel flow. Higher yield stress promoted lower free flow properties. However, excessively high yield stress can be detrimental to the gel's ability to move, when centrifuged. In effect, provisions for reduced free flow formulations go contrary to the gel's functional ability to move during centrifugation.

Yield stress values have also been shown to affect the form and stability of the barrier. Before centrifugation, the collected gel tube-blood specimens must be maintained in a transitory condition, for the predetermined time period, to allow for clotting and contraction of the blood clot to take place and to prevent the formation of fibrinogen in the serum. After centrifugation, the blood clot is further compacted to the bottom of the tube. The blood clot does possess some elastic properties and would naturally tend to expand to its pre-centrifuged condition, thereby exerting an expansive force on the gel barrier which could effectively disturb the barrier form. Some gel systems overcome this problem simply by increasing polymer viscosity, which has also proven effective at maintaining barrier stability. The main drawback to this provision is that the resulting gel is very difficult to process and dispense.

SUMMARY OF THE INVENTION

Accordingly, the objects of the present invention are to eliminate the above-mentioned disadvantages of the prior art and to provide a blood separation sealant having an ideal separation ability and higher reliability and capable of decreasing the overall material volume and of significantly reducing the processing cost.

In accordance with the present invention, there is provided a serum separating sealant having a specific gravity at 20° C. of 1.035 to 1.065, a viscosity of 100 to 400 Pa.S and a yield stress of 100 to 400 dyne/cm$^2$ and comprising.
(A) 100 parts by weight of a polymer having a specific gravity at 20° C. of 0.94 to 1.06 and a viscosity of 10 to 140 Pa.S, derived from an alkyl acrylate or alkyl methacrylate monomer having the formula (I):

wherein $R^1$ denotes H or $CH_3$, $R^2$ denotes an alkyl group having 1 to 18 carbon atoms;
(B) 0.5 to 10 parts by weight of at least one component selected from the group consisting of silica and bentonite; and
(C) 0.01 to 2 parts by weight of at least one surfactant selected from the group consisting of:
 (C-1) fluorocarbon-based surfactants;
 (C-2) polyester modified alkylpolysiloxane based surfactants; and
 (C-3) polyether modified alkylpolysiloxane based surfactants and, optionally, comprising, based upon 100 parts by weight of the polymer (A),
(D) 0.01 to 1 parts by weight of at least one component selected from the group consisting of titanium dioxide and calcium carbonate; and
(E) 0.02 to 1 parts by weight of a titanium based coupling agent.

DESCRIPTION OF THE PREFERRED EMBODIMENTS

According to the present invention, it has been found that the excellent resistant capability against the above-mentioned expansion of the blood clot as the yield value or thixotropicity is increased is achieved.

The serum separation sealant according to the present invention comprises as the essential constituents, the components (A), (B) and (C) as mentioned above.

The polymers usable as the component (A) in the present invention are those obtained by polymerizing the alkyl acrylate and/or alkyl methacrylate (hereinbelow referred to simply as "acryl polymer") and having a specific gravity at 20° C. of 0.94–1.06, preferably 1.030–1.045 and a viscosity of 10–140 Pa.S, preferably 50–100 Pa.S. The preferable number average molecular weight of the above-mentioned acryl polymer is 4000–12000. These acryl polymers have advantages that the monomers therefore are readily available and at low costs. Furthermore, since the specific gravity and viscosity of these polymers can be readily adjustable, a wide range of the viscosity-specific gravity combination can be achieved depending upon the needs of the consumers. Furthermore, a uniform resin can be obtained without necessitating complicated operations, unlike the conventional polymers, and no floating on the separated serum is formed.

The polymerizable monomers usable for the preparation of the polymer (1) of the component (A) constituting the serum separation sealant according to the present invention are so-called alkyl acrylates or alkyl methacrylates. Examples of such monomers are methyl(meth)acrylate (i.e., this means methyl acrylate or methyl methacrylate, the same as hereinbelow), ethyl (meth)acrylate, n-butyl(meth)acrylate, i-butyl(meth)acrylate, 2-ethylhexyl(meth)acrylate, lauryl(meth)acrylate, tridecyl(meth)acrylate, and stearyl (meth)acrylate. Among these, n-butyl(meth)acrylate or ethylhexyl(meth)acrylate or copolymers obtained from the combined use of these monomers are preferable, because these polymers have an appropriate viscosity, are easy to handle, and are capable of readily dispersing silica or the like therein when silica or the like is dispersed to control the specific gravity, the viscosity and the like.

Furthermore, in addition to the monomer represented by the formula (I), any copolymerizable monomer (i.e., "additional monomer" hereinafter) can be used, in combination therewith. Typical examples of such copolymerizable monomers are ethylene glycol diacrylate, propylene glycol diacrylate, neopentyl glycol diacrylate, 1,6-hexanediol diacrylate, diethylene glycol diacrylate, triethylene glycol diacrylate, tetraethylene glycol diacrylate, ethylene glycol dimethacrylate, propylene glycol dimethacrylate, neopentyl glycol dimethacrylate, 1,6-hexanediol dimethacrylate, diethylene glycol dimethacrylate, 1,2,3-propanetriol di(meth)acrylate, divinylbenzene and the like when the additional monomer is used, the weight ratio of the polymerizable monomer represented by the formula (I) and the additional monomer in terms of the solid content is preferably 99.9/0.1 to 90/10, more preferably 99.9/0.1 to 95/5.

The formation of gelatinous floating material can be controlled by making the specific gravity of the polymer higher than the specific gravity (i.e., 1.025–1.032) of the serum. However, when a polymer having a lower specific gravity is used, it is effective that the polymer can be uniformly mixed with the addition of a dispersing agent in a liquid polymerization reaction mixture, whereby the dispersion of the mixture having a specific gravity higher than that of the serum can be kept at the most optimum condition. Regarding the shelf life, high viscosity was effective at maintaining the solid additives in suspension and preventing dissolution of the mixture. This is especially important for gels using low specific gravity polymers.

The silica and/or bentonite to be used as the component (B) of the serum separation sealant according to the present invention are those as used for gel-network forming and/or as a specific gravity control agent. Although there are no specific limitations to the kinds of silica and bentonite usable in the present invention, fumed silica such as "Aerosil" (Trade mark) available from Degussa can be preferably used. Although there are no specific limitations to the particle size of the silica, the preferable particle size is 50 m$\mu$ or less, more preferably 5 to 40 m$\mu$.

On the other hand, any bentonite can also be used in the present invention. For example, "BENTONE" (Trade mark) (smectite/hectorite) available from NL Chemicals can be preferably used. The silica and/or bentonite are used in an amount of 0.5 to 10 parts by weight, preferably 1 to 5 parts by weight, based upon 100 parts by weight of the acrylic polymer (A). When the amount of the component (B) is less than 1 part by weight, the desired structural viscous properties cannot be obtained, and therefore, the free movability becomes high. Contrary to this, when the amount of the component (B) is more than 10 parts by weight, the specific gravity becomes high and the movability of the barrier formation is decreased.

As the component (C) of the serum separation sealant according to the present invention, at least one surfactant selected from the group consisting of fluorocarbon based surfactants, polyester modified alkylpolysiloxane based surfactants, and polyether modified alkylpolysiloxane based surfactants is formulated in an amount of 0.01 to 2 parts by weight, preferably 0.05 to 1.8 parts by weight, based upon 100 parts by weight of the above-mentioned acryl polymer (A). When the formulation amount is less than 0.01 part by weight, it is difficult to obtain the necessary viscosity, and therefore, the free movability becomes high. Contrary to this, when the formulation amount is more than 2 parts by weight, the viscosity is increased and the movability of the barrier formation is decreased.

The fluorocarbon-based surfactants (C-1) usable as the component (C) of the present invention may include, for example, those having the formula (II):

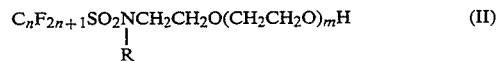

$$C_nF_{2n+1}SO_2\underset{R}{N}CH_2CH_2O(CH_2CH_2O)_mH \quad (II)$$

wherein n is an integer of 1–20, m is an integer of 10–20 and R denotes an alkyl group, preferably having 1 to 20 carbon atoms.

Examples of such surfactants are MEGAFAC. F142/F144 (Trade mark) by Dainippon Ink and Chemicals, Inc. and FLUORAD FC170C. (Trade mark) by Sumitomo 3M Co., Ltd.

The polyether modified alkylpolysiloxane based surfactants (C-3) usable as the component (C) of the present invention may include, for example, those having the formula (III):

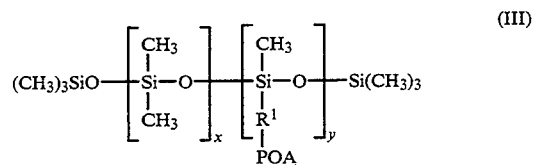

wherein $R^1$ denotes an alkyl group, preferably having 1 to 20 carbon atoms, POA denotes a polyoxyalkyl (R—O—$R^1$) group, x is an integer of 8–120, y is an integer of 8–120, and R is an alkyl group, preferably having 1 to 20 carbon atoms.

Examples of such polyether modified alkylpolysiloxane based surfactants (C-3) are "Toray-Dow Corning SH190, 192, SF 3748, SH 3746, SH 3749, SH 3771, SH 8400, SH 8700 (Trade mark) available from Toray-Dow Corning K.K.

The polyester modified alkylpolysiloxane based sulfonates (C-2) usable as the component (C) of the present invention may include, for example, those having the formula (IV):

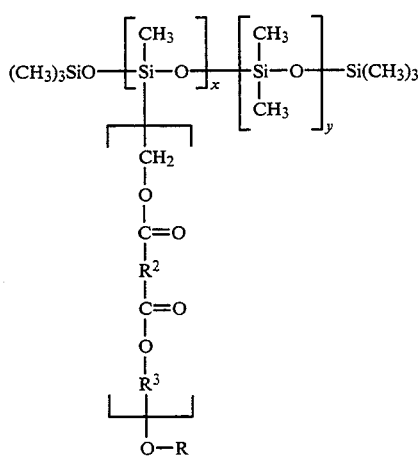

wherein R denotes hydrogen or an alkyl group, preferably having 1 to 20 carbon atoms, $R^2$ and $R^3$ denote independently an alkyl group, preferably having 1 to 20 carbon atoms, and x and y are independently 8 to 120.

Examples of such polyester modified alkylpolysiloxane based surfactants (C-2) are BYK310 or 370 (Trade mark) available from BYK Chemic K.K.

The serum separation sealant according to the present invention may optionally include, in addition to the essential constituents (A), (B) and (C), 0.01 to 1 part by weight, preferably 0.05 to 0.8 parts by weight, based on 100 parts by weight of the component (A), of titanium dioxide and/or calcium carbonate as the optional component (D) and 0.02 to 1 part by weight, preferably 0.1 to 0.8 parts by weight, based on 100 parts by weight of the component (A), of a titanium based coupling agent (E). When the amount of the component (D) is out of the above-mentioned range, it becomes difficult to obtain the desired specific gravity. When the amount of the titanium based coupling agent of the component (E) is less than 0.02 parts by weight, the viscosity is increased and the desired movability of barrier formation is difficult to obtain. Examples of the titanium based coupling agents of the component (E) are the following various Prenact materials (Trade mark) available from Ajinomoto Co., Ltd.

KRTTS (isopropyl-triisostearyltitanate)

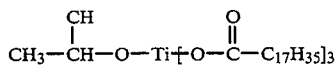

KR-9S (isopropyltridodecylbenzene sulfonyl titanate)

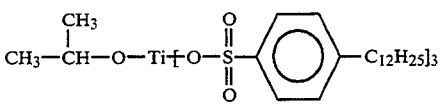

KR-12(isopropyltri(dioxylphosphate)titanate

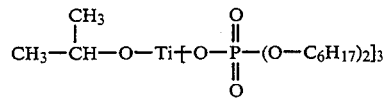

These titanium based coupling agent improve the affinity of the polymer with the filler and the dispersibility by chemically associating with the acrylic polymer and the inorganic portion, whereby the dissolution of the mixture is prevented.

The serum separation sealant has a specific gravity at 20° C. of 1.035 to 1.065, preferably 1.04 to 1.055, a viscosity of 100 to 400 Pa.S, preferably 140 to 320 Pa.S and a yield stress of 100 to 400 dyne/$cm^2$ preferably 150 to 300 dyne/$cm^2$.

Although high viscosities are most effective at maintaining a stable barrier, they make it difficult for directly dispensing to the blood tube and for maintaining a stable barrier after centrifugal separation. To add the barrier strength and especially prevent free flow, adjustment of yield stress to a range of 100 to 400 dynes/$cm^2$ was found to be necessary. The higher the yield stress, the stronger the barrier. However, yield stresses greater than 400 dynes/$cm^2$ tend to inhibit movement, making the gelatinous material less reliable. In order to achieve the desired movement, the gel's specific gravity should be between that of the serum and the blood clot. A typical range should be within the above range. Lower specific gravity values can improve movement, due to the increased buoyant forces exerted on the gel body.

The nature of the acrylic polymer and other raw materials allow for easy adjustments of these properties. Listed in Table 1 are the parameters which could be adjusted to effectively control gel properties. The extensive range of provisions make it possible to create a wide array of gels with varying properties. This is especially prevalent when an acrylic copolymer is used as opposed to a homopolymer. For such polymers, specific gravity can be adjusted over a wide range without affecting other properties such as yield stress. Thus, network former content or yield stress, for example, can be controlled independently without affecting specific gravity.

TABLE 1

GEL PROPERTY-ADJUSTMENT PARAMETER

| GEL PROPERTY | ADJUSTMENT PARAMETERS | | | | |
|---|---|---|---|---|---|
| | POLYMER (A) VISCOSITY | POLYMER (A) SPECIFIC GRAVITY | NETWORK FORMER (B) CONTENT | THIXOTROPIC AGENT (C) CONTENT | FILLER (D) CONTENT |
| VISCOSITY | +++ | +− | ++ | +++ | +− |
| YIELD STRESS | − | − | +++ | +++ | − |
| SPECIFIC GRAVITY | +− | +++ | +++ | − | +++ |

+++: HIGHLY EFFECTIVE
++: EFFECTIVE
+: SOME EFFECT
+−: LITTLE OR NO EFFECT
−: NO EFFECT

EXAMPLES

Examples of the present invention will be explained below, but the technical scope of the present invention is not intended to be limited by these Examples. In the following Examples, "parts" and "%" indicate parts or percent by weight unless otherwise indicated.

Example 1 (Comparative)

The separation of human blood was effected in a gel tube by using a serum separation sealant comprising a copolymer of ethyl acrylate and lauryl methacrylate (mole ratio=1:1) and having a specific gravity of 1.04 and a viscosity of 60 Pa.S. However, these sealants exhibited a Newtonian viscosity phenomenon and exhibited an excessive free flow ability, and therefore, were not practically usable at all. The yield stress of this sealant was zero. When the gel tube was laid on its side, the polymer flowed and coated the upper tube wall, rendering the whole unit useless.

Example 2 (Comparative)

To overcome the free flow problems of the sealant according to Example 1, a copolymer of 15 parts of lauryl methacrylate, 24 parts of n-butyl acrylate, 60 parts of ethyl hexyl methacrylate and 1 part of ethylene glycol dimethacrylate and having a specific gravity of 0.950 and a viscosity of 20 Pa.S was used as a sealant. Added to 100 parts of this polymer was fine silica powder in an amount of up to 20 parts by weight and a sealant having a specific gravity of 1.05 and a viscosity of 250 Pa.S was produced. Addition of silica powder imparted thixotropy to the sealant and the yield stress was 20 to 50 dynes/cm$^2$. The production of such a sealant involved the pre-mixing of the components with a mechanical mixer, the dispersion was formed through a roll mill by 4 passes, and then air bubbles were removed by vacuum mixing. The final product thus obtained involves a mixture of constituents of acryl polymer and network former/fillers, which are immiscible with each other. Therefore appropriate dispersion condition was especially difficult to obtain due to the high particle content.

Test results using the above-produced sealant showed a noticeable decrease in free flow and improved barrier formability. However, because of the high silica content, the gel tended to harden with time, making it unreliable after long term storage (e.g., 180 days). Moreover, in spite of the high aerosil content, the thixotropy was still relatively low and a further decrease in free flow was desirable. It also demonstrated the presence of a noticeable amount of floating gel particles. This is the most common complaint voiced by users of a serum separation sealant as well as other similar units.

Examples 3–16 (Present Invention)

Various blood separation sealants according to the present invention were produced. The particulars of these sealants are shown in Tables 2 and 3. As the component (A), various polymers polymerized from n-butyl acrylate (NBA), ethylhexyl acrylate (EHA) and ethylene glycol dimethacrylate (EGDM) were used in the compositions shown in Tables 2 and 3. The viscosities and the specific gravities were as shown in Tables 2 and 3.

As the component (B), silica such as Aerosil (Trademark) R805, R812, R972, A130 and OX50 and bentone (i.e., B-38 available from NL Chemicals Co.) were used in an amount shown in Tables 2 and 3. As the component (C), SH190 (i.e., polyether modified alkyl polysiloxane based surfactant available from Toray-Dow Corning Silicone K.K.), BYK370 (i.e., polyester modified alkyl polysiloxane-based surfactant) F144, F-177 (i.e., fluorocarbon based surfactant) and FC170C (i.e., fluorocarbon based surfactant available from Sumitomo 3M Co., Ltd.) were used in an amount shown in Tables 2 and 3. Furthermore, as the optional component (D), calcium carbonate (CaCO$_3$) and titanium dioxide (TiO$_2$) were used and as the optional component (E), and a thitanin based coupling agent, KRTTS, KR-9S and KR-12 (i.e., PRENACT of Ajinomoto Co., Ltd.) was used in an amount shown in Tables 2 and 3.

As mentioned above, silica and/or bentone are a network former and the alkylpolysiloxane and/or fluorocarbon based surfactants were included to enhance the viscosity of the sealant. This allowed for the significant reduction in network former content, from a maximum concentration of 30 parts down to less than 12 parts by weight. This reduced concentration made the production process much easier to achieve. For example, the roll milling can be reduced to two passes or less, or eliminated altogether. A titanium coupling agent can also be incorporated in the formulation to promote improved dispersion of the network former/filler contents. The production of the acrylic polymer generally involves the dropwise addition of the monomer components, to 30–60 parts by weight of an appropriate solvent (e.g., xylene, toluene). After the completion of monomer addition, the mixture is aged to allow for the complete reaction and is then evaporated to remove the solvent.

The formulation and various physical properties and the like are shown in Tables 2 and 3. The units of the viscosity and the yield stress in the Tables are Pa.S and dyne/cm$^2$, respectively.

Example 17 (Comparative)

In preparing compositions of the comparative example, the silicone fluid as a polymer was a dimethylpolysiloxane, made available by Dow Corning Corp. and identified as a 200 Series Silicone Fluid. It had a viscosity of about 12,500 centistokes at 25° C. and a specific gravity of 0.975. The silica particles consisted of very finely divided particles having a surface area of about 110 m$^2$/g and a specific gravity of about 2.2. The silica particles were obtained from Degussa, Inc., and identified by the designation D.17. The silicone fluid and silica particles were initially mixed together in the indicated amounts by pre-mixing to obtain a gel-like composition having an initial viscosity of about 200,000. The component (C), SH 190 (i.e., polyether modified alkyl polysiloxane based surfactant available from Toray-Dow Corning Silicone K.K.) was titrated into the two-component system in an amount shown below to obtain a viscosity of about 141 Pa.S, a yield stress of 213 dyne/cm$^2$ and a specific gravity of 1.042.

| Components | Parts by weight |
| --- | --- |
| Silicone fluid | 100 |
| Silica | 15 |
| SH 190 | 0.0173 |

TABLE 2

| | Example | | | | | |
|---|---|---|---|---|---|---|
| | 3 | 4 | 5 | 6 | 7 | 8 |
| NBA | 80.00 | 59.00 | 81.00 | 14.00 | 100 | 14.00 |
| EHA | 19.00 | 40.00 | 19.00 | 85.00 | — | 85.00 |
| EGDM | 1.00 | 1.00 | — | 1.00 | — | 1.00 |
| Property of Component (A) | | | | | | |
| VISCOSITY (Pa.S) | 80 | 120 | 90 | 130 | 130 | 100 |
| SPECIFIC GRAVITY | 1.031 | 1.017 | 1.035 | 0.990 | 1.050 | 0.990 |
| Component (B) | | | | | | |
| R805[1] | — | — | — | — | 0.50 | — |
| R812[1] | — | — | — | 9.40 | — | — |
| R972[1] | — | — | 0.20 | — | — | 7.10 |
| A130[1] | 4.30 | 3.00 | 2.60 | — | 2.90 | 2.80 |
| OX50[1] | — | 2.00 | — | — | — | — |
| B-38[2] | — | 1.50 | — | — | 0.25 | — |
| Component (C) | | | | | | |
| SH190[3] | 1.25 | 1.00 | 0.60 | 1.00 | 0.25 | — |
| BYK370[4] | — | — | — | — | — | 1.20 |
| Component (D) | | | | | | |
| $CaCO_3$ | — | 0.20 | 0.20 | 0.50 | — | 0.50 |
| Component (E) | | | | | | |
| KRTTS[5] | — | — | — | 0.06 | 0.08 | 0.20 |
| Property of gel | | | | | | |
| VISCOSITY (Pa.S) | 229 | 311 | 189 | 355 | 280 | 311 |
| YIELD STRESS | 275 | 300 | 210 | 250 | 225 | 360 |
| SPECIFIC GRAVITY | 1.054 | 1.050 | 1.052 | 1.040 | 1.065 | 1.045 |
| MANUFACTURING METHOD | premix + roll mill | premix + roll mill | mix only | premix + roll mill | premix + roll mill | premix + roll mill |

NOTE:
[1]AEROSIL TM (DEGUSSA); [2]BENTONE; [3]TORAY-DOW SILICONE; [4]BYK CHEMIE; [5]PRENACT-(AJINOMOTO);

TABLE 3

| | Example | | | | | | | |
|---|---|---|---|---|---|---|---|---|
| | 9 | 10 | 11 | 12 | 13 | 14 | 15 | 16 |
| Component (A) | | | | | | | | |
| NBA | 75.00 | 77.00 | 81.00 | 78.00 | 78.00 | 78.00 | 78.00 | 77.00 |
| EHA | 25.00 | 23.00 | 19.00 | 22.00 | 22.00 | 22.00 | 22.00 | 23.00 |
| EGDM | 0.50 | 0.20 | 1.30 | 1.00 | — | — | — | 0.20 |
| Property of Component (A) | | | | | | | | |
| VISCOSITY (Pa.S) | 77 | 70 | 177 | 90 | 100 | 90 | 100 | 70 |
| SPECIFIC GRAVITY | 1.030 | 1.032 | 1.030 | 1.025 | 1.033 | 1.033 | 1.033 | 1.032 |
| Component (B) | | | | | | | | |
| R805[1] | — | — | 3.65 | 3.00 | — | — | — | — |
| R972[1] | 1.00 | 1.80 | — | — | 1.00 | 1.00 | 1.00 | 1.80 |
| A130[1] | 2.70 | 2.70 | — | — | 2.60 | 2.60 | 2.60 | 2.70 |
| A300[1] | — | — | — | 1.50 | — | — | — | — |
| SD3[2] | — | — | — | 0.25 | — | — | — | — |
| Component (C) | | | | | | | | |
| SH190[3] | 0.50 | 2.00 | 0.50 | — | — | — | 0.10 | 2.00 |
| F144[1] | — | — | — | 0.50 | — | — | — | — |
| F177[4] | — | — | — | — | 0.25 | — | 0.5 | — |
| FC170C[5] | — | — | — | — | — | 0.25 | — | — |
| Component (D) | | | | | | | | |
| $CaCO_3$ | — | — | 0.20 | — | 0.20 | 0.20 | 0.20 | 0.10 |
| $TiO_2$ | 0.02 | 0.02 | — | — | — | — | — | 0.01 |
| Component (E) | | | | | | | | |
| KR-9S[6] | 0.25 | — | — | — | — | — | — | — |
| KR-12[6] | — | 0.25 | — | — | — | — | — | 0.25 |
| Property of gel | | | | | | | | |
| VISCOSITY (Pa.S) | 145 | 150 | 295 | 247 | 194 | 196 | 200 | 166 |
| YIELD STRESS | 100 | 110 | 125 | 275 | 250 | 240 | 250 | 115 |
| SPECIFIC GRAVITY | 1.050 | 1.049 | 1.050 | 1.050 | 1.052 | 1.052 | 1.052 | 1.056 |
| MANUFACTURING METHOD | pre-mix + | pre-mix + | pre-mix + | pre-mix + | pre-mix + | pre-mix + | pre-mix + | pre-mix + |

TABLE 3-continued

| | | | Example | | | | |
|---|---|---|---|---|---|---|---|
| 9 | 10 | 11 | 12 | 13 | 14 | 15 | 16 |
| roll mill | roll mill | roll mill | roll mill | roll mill | roll mill | roll mill | roll mill |

NOTE:
[1]AEROSIL ™ (DEGUSSA); [2]BENTONE; [3]TORAY-DOW SILICONE; [4]DAINIPPON INK AND CHEMICACS; [5]SUMITOMO 3M
[6]PRENACT (AJINOMOTO);

Evaluation Test of Sealant of Examples 1 to 17

Viscosities of all samples were measured using an EHD type cone and plate viscometer at variable shear rates. Viscosities with their corresponding shear rates can be used to estimate yield stress according to Casson plot theory.

All samples were subjected to comparative evaluation for free flow wherein the procedure included the following steps:

1.) 1.5 ml of gel dispensed into 10 ml glass tubes.
2.) Dispensed gel tubes are maintained in an upright position for a time period of 3 minutes.
3.) The initial gel position is marked and the gel tube is secured resting on its side.
4.) After 1 day, the flow distance from the initial position is measured.

Flow distance of each gel were rated as follows:
+ + +: x<5 mm
+ +: 5 mm≦x<10 mm
+: 10 mm≦x<15 mm
+ −: 15 mm≦x≦20 mm
−: >20 mm All gel samples were subjected to human blood test evaluations, whereby the movement during centrifugation (movement), the gel barrier formation (barrier formation), the barrier stability after one day (barrier stability), the existence of gel material on serum surface were rated and an amount of the blood clot adhered to the surface of the gel (blood clot adhesion: no adhesion on the sealant was excellent) in the following manner:
+ + +: Excellent
+ +: Very good
+: Acceptable
+ −: Fair
−: Poor Before the actual test, tube materials containing 1.8 ml of gel were stored at 60° C. for 1 month, as a way of simulating normal shelf aging of over 1 year. Approximately 8 ml of blood were collected in each tube and allowed to clot for up to 1 hr. The samples were then centrifuged at 800 G for 10 min. Normal procedures usually involve centrifuging ≧1300 G for 10 min. However, to ensure reliability, a stricter centrifuging standard of 800 G×10 minutes was chosen.

The results are shown in Table 4.

TABLE 4

| | Evaluation Results | | | | | |
|---|---|---|---|---|---|---|
| | HUMAN BLOOD TEST EVALUATION AFTER PRIOR AGING @ 60° C. × 1 MONTH | | | | | |
| EXAMPLE | FREE FLOW | MOVEMENT 800 G × 10 min | BARRIER FORMATION | BARRIER STABILITY | FLOATING GEL | BLOOD CLOT ADHESION |
| 1 | − | + + + | + − to + | − | − to + | − |
| 2 | + − | − to + | − to + | − to + | − | + + |
| 3 | + + + | + + + | + + + | + + + | + + + | ± |
| 4 | + + + | + to + + + | + + | + + + | + to + + | + |
| 5 | + + | + + + | + + | + + + | + + + | ± |
| 6 | + + | + + | + + | + + + | + to + + | + + |
| 7 | + + | + + + | + + + | + + + | + + + | ± |
| 8 | + + + | + + | + + | + + + | + | + + |
| 9 | + | + + + | + + | + + | + + + | ± |
| 10 | + | + + + | + + | ÷ + | + + + | ± |
| 11 | + | + + + | + + | + + + | + + + | ± |
| 12 | + + + | + + + | + + + | + + + | + + | ± |
| 13 | + + | + + + | + + | + + + | + + + | ± |
| 14 | + + | + + + | + + + | + + + | + + + | ± |
| 15 | + + | + + + | + + + | + + + | + + + | ± |
| 16 | + | + + + | + + | + + | + + + | ± |
| 17 | + + | + + | + | + + | − | ± |

Test evaluations indicate that the present invention, represented by Examples 3 to 16, shows a noticeable improvement in overall performance qualities, when compared with the comparative samples of Examples 1 and 2 and Example 17. Most importantly, reliability in terms of the movement and the barrier stability was noticeably improved despite the extreme temperature storage. These improvements were achieved without the need of special provisions such as insertion of an "Energizer" or special gel dispensing procedures to promote movement, as outlined in the prior art. Moreover, practical characteristics such as free flow and floating gel materials were noticeably decreased or eliminated altogether. Example 5, which utilized only planetary mixing in its manufacture, demonstrated it is possible to simplify the production processing and still retain the same performance qualities as in the other Examples. Gels similar to Example 2 (Comparative Example), by virtue of high silica content, made it impossible to conduct any type of simplification. A high shearing action generated by the roll mill was compulsory for manufacture.

As mentioned before, the present invention allows for easy adjustability in polymer or filler/network former content to achieve optimum qualities. A representative formulation in accordance with Example 3-16 was produced and further evaluated under the regimen of Therapeutic Drug Monitoring (TDM) procedures. The test involved comparisons of drug recovery from blood samples, over a period of 1 hr. to 3 days, using the composite gel formula. The drugs monitored included digoxin, disopyramide, lidocaine, procainamide, quinidine, gentamicin, acetominaphen, valproic acid, phenytoin, carbamazepine, and phenobarbital. Analysis showed a very high standard of recovery, demonstrating the gel materials inertness with respect to these drugs. General assay for electrolytes and biochemical materials also showed no influences on analytical data, which also demonstrated the gels inertness with respect to the blood itself. Composite gel samples were also subjected to gamma ray radiation at 1.5 Mrad, showing little or no effect on rhoelogical behavior and performance qualities.

We claim:

1. A serum separation sealant having a specific gravity at 20° C. of 1.035 to 1.065, a viscosity of 100 to 400 Pa.S at 20° C. and a yield stress of 100 to 400 dyne/cm² at 20° C. and comprising:
   (A) 100 parts by weight of a polymer having a specific gravity at 20° C. of 0.94 to 1.06 and a viscosity of 10 to 140 Pa.S, derived from an alkyl acrylate or alkyl methacrylate monomer having the formula (I):

wherein R¹ denotes H or CH₃, R² denotes an alkyl group having 1 to 18 carbon atoms;
   (B) 0.5 to 10 parts by weight of at least one component selected from the group consisting of silica and bentonite; and
   (C) 0.01 to 2 parts by weight of at least one surfactant selected from the group consisting of:
      (C-1) fluorocarbon-based surfactants; and
      (C-2) polyester modified alkylpolysiloxane based surfactants.

2. A serum separation sealant as claimed in claim 1, wherein the surfactent (C) is at least two surfactants selected from the group consisting of the surfactants (C-1) and (C-2).

3. A serum separation sealant as claimed in claim 1, further comprising: based upon 100 parts by weight of the polymer (A),
   (D) 0.01 to 1 parts by weight of at least one component selected from the group consisting of titanium dioxide and calcium carbonate; and
   (E) 0.02 to 1 parts by weight of a titanium based coupling agent.

4. A serum separation sealant as claimed in claim 1, wherein the component (A) is a copolymer of (i) the alkyl acrylate or methacrylate monomer having the formula (I) and (ii) a comonomer copolymerizable with said alkylacrylate or methacrylate monomer having the formula (I) at a mole ratio of (i)/(ii) of 99.9/0.1 to 90/10.

5. A serum separation sealant as claimed in claim 1, wherein the amount of the component (B) is 1–5 parts by weight, based on 100 parts by weight of the component (A).

6. A serum separation sealant as claimed in claim 1, wherein the amount of the component (C) is 0.05 to 1.8 parts by weight, based on 100 parts by weight of the component (A).

7. A serum separation sealant as claimed in claim 3, wherein the amount of the component (D) is 0.05 to 0.8 parts by weight, based on 100 parts by weight of the component (A).

8. A serum separation sealant as claimed in claim 3, wherein the amount of the component (E) is 0.1 to 0.8 parts by weight.

9. A serum separation sealant as claimed in claim 1, wherein the component (C) is a component (C-1) having the formula (II):

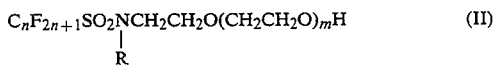

wherein n is an integer of 1–20, m is an integer of 10–20 and R denotes an alkyl group.

10. A serum separation sealant as claimed in claim 1, wherein the component (C) is a component (C-2) having the formula:

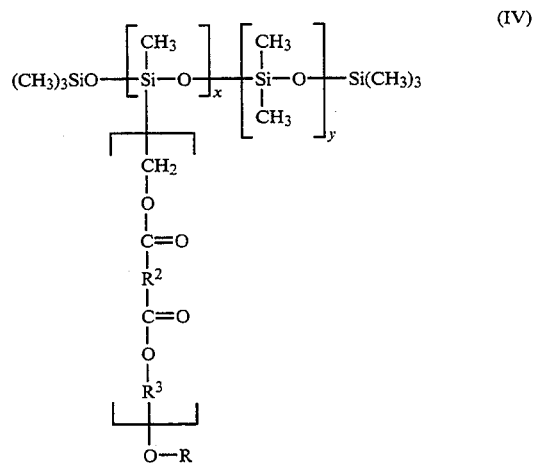

wherein R denote hydrogen or an alkyl group, R² and R³ denotes independently an alkyl group, and x and y are independently 8 to 120.

11. A serum separation sealant as claimed in claim 3, wherein the component (E) is at least one member selected from the group consisting of isopropyltriisostearyl titanate, isopropyltridodecylbenzene sulfonyl titanate and isopropyltri(dioxylphosphate) titanate.

12. A serum separation sealant as claimed in claim 1, having a specific gravity at 20° C. of 1.04 to 1.055, a viscosity of 140 to 320 Pa.S at 20° C. and a yield strerss of 150 to 300 dyne/cm² at 20° C.

* * * * *